United States Patent
Haase et al.

(10) Patent No.: US 11,172,896 B2
(45) Date of Patent: Nov. 16, 2021

(54) DRUG CONCENTRATION DETERMINATION AFTER TRANSARTERIAL CHEMOEMBOLIZATION WITH DIFFERENT SIZED DRUG-ELUTING MICROSPHERE BEADS

(71) Applicant: KONINKLIJKE PHILIPS N.V., Eindhoven (NL)

(72) Inventors: Christian Haase, Hamburg (DE); Dirk Schaefer, Hamburg (DE); Eberhard Sebastian Hansis, Hamburg (DE); Tobias Klinder, Uelzen (DE); Michael Grass, Buchholz in der Nordheide (DE); Ming De Lin, New Haven, CT (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 549 days.

(21) Appl. No.: 15/551,925

(22) PCT Filed: Dec. 4, 2015

(86) PCT No.: PCT/EP2015/078737
§ 371 (c)(1),
(2) Date: Aug. 18, 2017

(87) PCT Pub. No.: WO2016/146214
PCT Pub. Date: Sep. 22, 2016

(65) Prior Publication Data
US 2018/0035960 A1 Feb. 8, 2018

Related U.S. Application Data

(60) Provisional application No. 62/134,639, filed on Mar. 18, 2015.

(30) Foreign Application Priority Data

May 6, 2015 (EP) .................................. 15166519

(51) Int. Cl.
A61B 6/00 (2006.01)
A61B 6/03 (2006.01)
(Continued)

(52) U.S. Cl.
CPC .............. *A61B 6/481* (2013.01); *A61B 6/032* (2013.01); *A61B 6/405* (2013.01); *A61B 6/4241* (2013.01);
(Continued)

(58) Field of Classification Search
CPC ......... A61B 6/481; A61B 6/032; A61B 6/405; A61B 6/4241; A61B 6/482; A61B 6/504; A61K 49/0419
See application file for complete search history.

(56) References Cited

U.S. PATENT DOCUMENTS 9,107,850 B2   8/2015   Fritz
2008/0102029 A1   5/2008   Fritz

FOREIGN PATENT DOCUMENTS

CN   101090710 A   12/2007
WO   WO2009014549 A1   1/2009
(Continued)

OTHER PUBLICATIONS

Deipolyi, Amy R., Rahmi Oklu, Shehab Al-Ansari, Andrew X. Zhu, Lipika Goyal, and Suvranu Ganguli. "Safety and efficacy of 70-150 µm and 100-300 µm drug-eluting bead transarterial chemoembolization for hepatocellular carcinoma." Journal of Vascular and Interventional Radiology 26, No. 4 (2015): 516-522 (Year: 2015).*
(Continued)

*Primary Examiner* — Carolyn A Pehlke
(74) *Attorney, Agent, or Firm* — Larry Liberchuk

(57) ABSTRACT

The present invention is directed towards a system and method for transarterial chemoembolization using differently sized drug-eluting microsphere beads filled with drugs and determining a delivered drug concentration using an imaging system.

16 Claims, 3 Drawing Sheets

(51) Int. Cl.
*A61K 49/04* (2006.01)
*A61M 5/00* (2006.01)
G16H 20/17 (2018.01)
G16H 30/20 (2018.01)

(52) U.S. Cl.
CPC .............. *A61B 6/482* (2013.01); *A61B 6/504* (2013.01); *A61K 49/0419* (2013.01); *A61M 5/00* (2013.01); *G16H 20/17* (2018.01); *G16H 30/20* (2018.01)

(56) References Cited

FOREIGN PATENT DOCUMENTS

| WO | 2010/007545 | 1/2010 | | |
|---|---|---|---|---|
| WO | 2011/014562 | 2/2011 | | |
| WO | WO-2013164725 A1 | * 11/2013 | ........... | G06T 7/0012 |
| WO | 2013/186661 | 12/2013 | | |

OTHER PUBLICATIONS

Vogl, Thomas J., Nagy NN Naguib, Nour-Eldin A. Nour-Eldin, Katrin Eichler, Stefan Zangos, and Tatjana Gruber-Rouh. "Transarterial chemoembolization (TACE) with mitomycin C and gemcitabine for liver metastases in breast cancer." European radiology 20, No. 1 (2010): 173-180.*

Mongan, John, Samira Rathnayake, Yanjun Fu, Runtang Wang, Ella F. Jones, Dong-Wei Gao, and Benjamin M. Yeh. "In vivo differentiation of complementary contrast media at dual-energy CT." Radiology 265, No. 1 (2012): 267-272.*

* cited by examiner

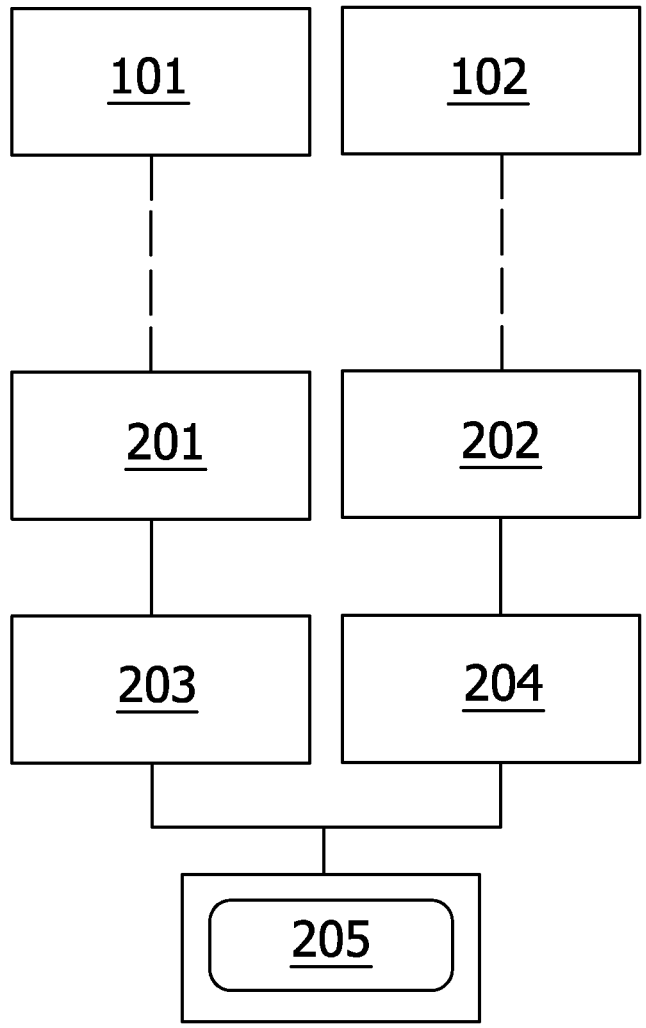
FIG. 5A
FIG. 5B
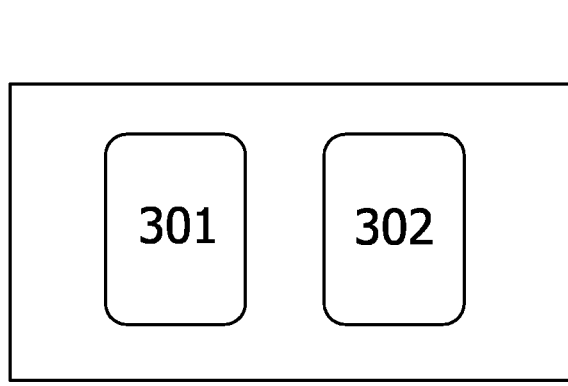
FIG. 6

DRUG CONCENTRATION DETERMINATION AFTER TRANSARTERIAL CHEMOEMBOLIZATION WITH DIFFERENT SIZED DRUG-ELUTING MICROSPHERE BEADS

CROSS REFERENCE TO RELATED APPLICATIONS

This application is the U.S. National Phase application under 35 U.S.C. § 371 of International Application No. PCT/EP2015/078737, filed Dec. 4, 2015, published as WO 2016/146214 on Sep. 22, 2016, which claims the benefit of European Patent Application Number 15166519.7 filed May 6, 2015 and U.S. Provisional Patent Application Number 62/134,639 filed Mar. 18, 2015. These applications are hereby incorporated by reference herein.

FIELD OF THE INVENTION

The present invention generally relates to a system for a transarterial chemoembolization (TACE) of a region of interst compring a tumor, a method for determining a delivered drug dose concentration in a region of interest comprising a tumor, a system for determining a drug concentration in a region of interest comprising a tumor after a transarterial TACE procedure, a computer program product for determining a drug concentration in a region of interest comprising a tumor after a transarterial TACE procedure and a TACE method.

BACKGROUND OF THE INVENTION

Liver cancer is one of the most common cancers worldwide. Treatment options are limited and clinical outcomes are generally poor with a median survival rate of less than one year. Given the fact that liver cancer (primary and metastatic) is primarily supplied by the hepatic artery and is generally confined to the liver, drug delivery directly into the hepatic artery has been shown to be effective. Transarterial chemoembolization (TACE) is an x-ray image guided, interventional oncology procedure in which chemotherapeutic drug is delivered from a catheter in the hepatic artery.

There has been a shift in chemotherapeutic drug delivery system from conventional lipiodol (cTACE) to drug-eluting microsphere beads (DEB-TACE). Drug-eluting microsphere beads (DEBs) are small beads with a shell and a core which may be loaded with a drug, such as chemotherapeutic agents, or other materials and which are capable of delivering the load in a reproducible manner to a region of interest that leads to lower levels of chemotherapy in plasma (less systemic exposure) and enhanced efficacy at the tumor site (more tumor kill).

An issue with TACE procedures is that it is very difficult to determine whether the intended drug dose actually reached the tumor. It is well known in chemotherapy medicine that a sufficient drug dose concentration is needed for tumor kill. With DEB-TACE some improvements were made regarding this issue. Since DEBs are usually radiolucent, in current clinical practice soluble x-ray contrast agent is mixed with DEBs to provide a surrogate marker of DEB deposition. However, it is known that the two materials can separate during delivery and thus provide false information about final DEB deposition location. As such, a new kind of DEB was developed that is inherently radio-opaque and thus provides direct visualization of bead deposition. In this case radio opacity in the target region is directly related to drug dose.

Over the years, the DEB's sizes have become smaller, in general from 100-300 microns to 75-150 microns in diameter. This smaller size allows for better tumor penetration. However, there are two limitations: smaller beads carry a smaller drug payload, and smaller beads are unable to embolize larger-sized tumor feeding vessels.

Also, it is known that the tumor core has a very different microenvironment than the tumor rim and different drugs are needed for each. With TACE procedures, including DEB-TACE, it is difficult to target and address both the core and rim effectively.

It would be highly desirable if a DEB-TACE method could target all areas in and around the tumor effectively with a reliable indication of drug delivery to each area.

SUMMARY OF THE INVENTION

Embodiments according to the present invention are directed to a system for a transarterial chemoembolization (TACE) of a region of interest comprising a tumor with an injector and an imaging system. The injector is arranged to introduce into the region of interest first drug-eluting microsphere beads containing at least a first drug and a first contrast agent and to introduce into the region of interest second drug-eluting microsphere beads containing at least a second drug and a second contrast agent. The imaging system is arranged to obtain a first image data set of the region of interest with at least a first x-ray radiation energy and a second image data set of the region of interest with at least a second x-ray radiation energy.

In a preferred embodiment the system further comprises a concentration determiner arranged to determine a first drug concentration from the first image data set and a second drug concentration from the second image data set.

In another preferred embodiment of the system the imaging system is a spectral computed tomography imaging system, preferably a spectral computed tomography system that is arranged to simultaneously obtain the first image data and second image data.

In another preferred embodiment of the system the first drug-eluting microsphere beads have a size such that they can not penetrate into tumor core vessels, and the second drug-eluting microsphere beads have a size such that they can penetrate into tumor core vessels.

In another preferred embodiment of the system the first drug is different from the second drug and/or wherein the first contrast agent is different from the second contrast agent.

In another preferred embodiment of the system the at least first x-ray radiation energy corresponds to a K-absorption edge of the first contrast agent and the at least second x-ray radiation energy corresponds to a K-absorption edge of the second contrast agent.

A further embodiment of the present invention is directed towards a method for determining a delivered drug dose concentration in a region of interest comprising a tumor, comprising the steps of obtaining a first image data set by imaging the region of interest with an x-ray imaging device operating at at least a first x-ray radiation energy; determining, from the first image data set, a first drug concentration delivered to the region of interest by first drug-eluting microsphere beads containing at least a first drug and a first contrast agent; obtaining a second image data set by imaging the region of interest with an x-ray imaging device operating at at least a second x-ray radiation energy; determining, from the second image data set, a second drug concentration delivered to the region of interest by second drug-eluting microsphere beads containing at least a second drug and a second contrast agent, wherein the first drug-eluting microsphere beads have a larger diameter than the second drug-eluting microsphere beads.

Other embodiments of the present invention are directed towards Computer program product for determining a drug concentration in a tumor after a transarterial chemoembolization procedure in which at least a first drug and a second drug were delivered to the region of interest and a transarterial chemoembolization procedure.

Still further aspects and embodiments of the present invention will be appreciated by those of ordinary skill in the art upon reading and understanding the following detailed description. Numerous additional advantages and benefits will become apparent to those of ordinary skill in the art upon reading the following detailed description of preferred embodiments.

BRIEF DESCRIPTION OF THE DRAWINGS

The present invention is illustrated by drawings of which
FIG. 5 shows a block diagram of a TACE procedure according to the present invention (5A) and a subsequent method for determining a delivered drug dose to a region of interest (5B).
FIG. 6 shows a schematic depiction of a kit-of-parts according to the present invention.

The invention may take form in various components and arrangements of components, and in various process operations and arrangements of process operations. The drawings are only for the purpose of illustrating preferred embodiments and are not to be construed as limiting the invention. To better visualize certain features may be omitted or dimensions may be not be according to scale.

DETAILED DESCRIPTION OF EMBODIMENTS

The invention will be illustrated by using spectral CT imaging, but another suitable multi-energy imaging device or other imaging device with which it is possible to discriminate between two materials could also be used. Furthermore, the present invention is directed to treatment of liver cancer, but the invention is also easily adaptable to other types of cancer and even to local drug treatment of other diseases.

Figure 1:
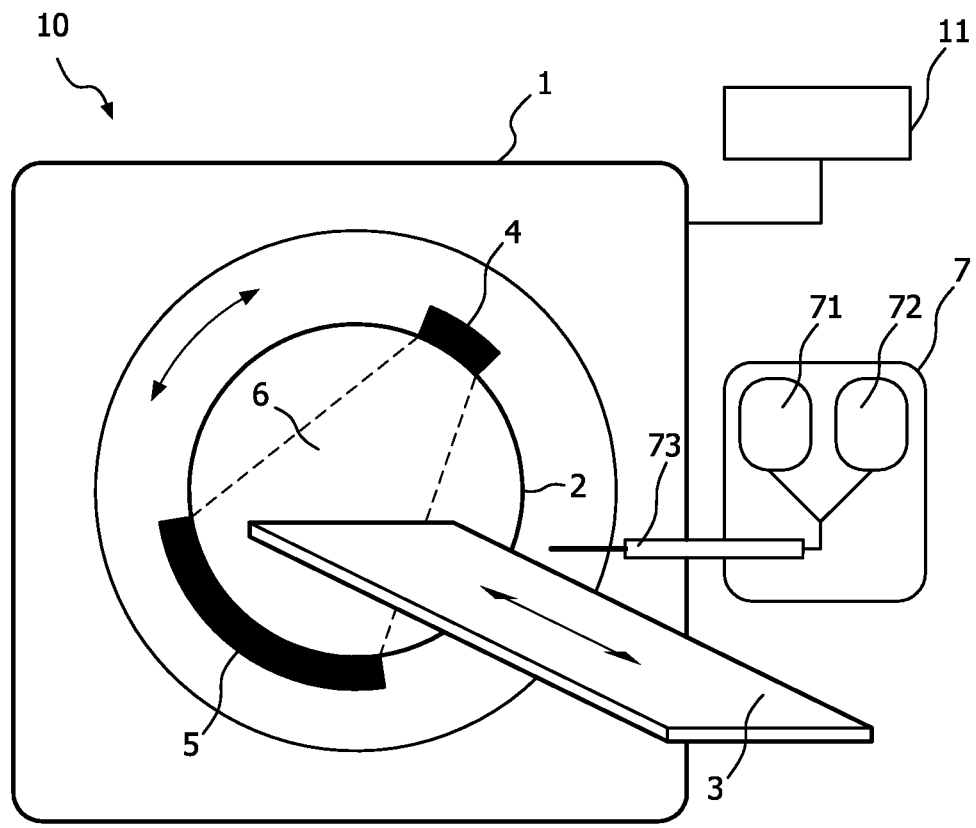
FIG. 1 shows a schematic representation of a system for transarterial chemoembolization according to the present invention.

FIG. 1 depicts a schematic representation of a system for transarterial chemoembolization 10 with two main components: an imaging system 1 and an injecting device 7.

In this example, the imaging system 1 is a computed tomography imaging system in which x-ray radiation is emitted in a radiation beam 6 from a source 4 towards a detector 5. Both are mounted opposite each other in a gantry 2, which is rotatable around an examination area. During an imaging procedure a subject, such as a patient, is placed on support 3 and translated trough the examination region and the radiation beam 6 while the gantry 2 rotates around the subject to obtain image data of the subject that may be reconstructed to two-dimensional or three-dimensional images.

This invention will be particularly explained using spectral CT (sometimes also referred to as dual source CT) as an example. In spectral CT x-ray radiation with different energies are detected and processed. This may be achieved by adapting the source to emit different wavelengths simultaneously or sequentially (e.g. in kVp switching x-ray sources) or by adapting the detector to detect different individual parts of an emitted wavelength spectrum. Different information may be derived from information obtained from high-energy x-ray radiation and low-energy x-ray radiation. For instance, materials may be distinguished from each other since different materials attenuate low and high energy radiation differently.

An often used imaging method in spectral (and conventional) CT imaging is k-edge imaging, usually of contrast agent materials. Due to the photoelectric absorptions of photons in atoms of an imaged material, such as a contrast agent, a sudden, non-linear increase in the attenuation coefficient of photons at an energy just above the binding energy of the K-shell electron occurs. This sudden increase is called the k-edge, which lies at different energies for different materials and therefore it can be separately detected by imaging with different radiation energies, such as in spectral CT imaging. And, as such, it is possible to identify different materials in a single imaging procedure.

FIG. 1 also shows a schematic depiction of an injecting device 7, which is drawn in a very basic form which only depicts examples of basic elements that could be part of such an injector. In this embodiment the injector 7 comprises a first DEB reservoir 71 and a second DEB reservoir 72, which both are connected to injector 73. The injector 73 may for instance be a catheter or a syringe to introduce the DEBs 81, 82 into a blood vessel, usually near the region of interest. According to the present invention the first DEB reservoir 71 is to be loaded for use with first DEBs and the second DEB reservoir is loaded with differently sized second DEBs. The skilled person would understand that the injector 73 can have many different designs and also that the DEB reservoirs 71, 72 can be connected to the injector in multiple manners. For instance, the first and second DEB reservoirs 71, 72 may be combined into one reservoir if the differently sized DEBs 81,82 are already premixed. The injecting device 7 is preferably placed close to the imaging system 1, but could also be placed away from the imaging system 1, or even in a separate room.

Figure 2:
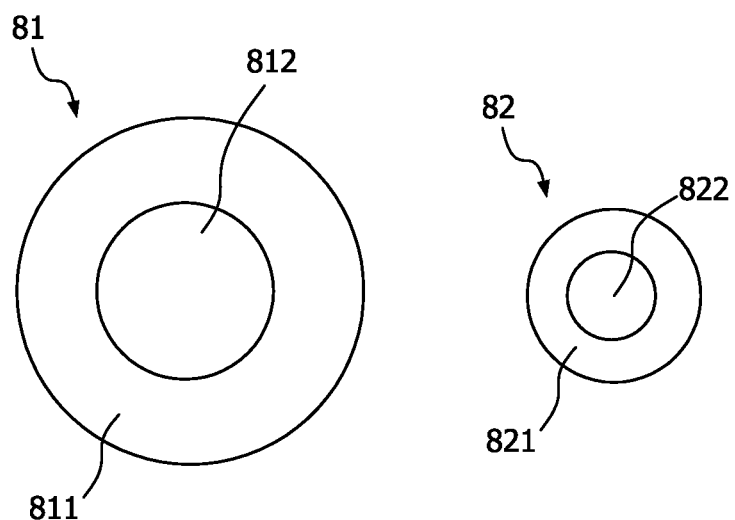
FIG. 2 shows a schematic representation of two differently sized drug-eluting microsphere beads.

FIG. 2 shows schematic depictions of two differently sized DEBs 81, 82.

DEBs are available in various sizes, usually ranging between 50 and 1000 microns. Both DEBs 81,82 comprise of a shell 811, 821 fully surrounding a central loading cavity 812, 822. The shell 811, 821 is preferably made of a biodegradable material, such as a biodegradable polymer, for instance a polyvinyl alcohol hydrogel. Shell thickness may vary for different DEB types and sizes. The central loading cavity 812, 822 is filled with a drug, such as for instance doxorubicin, which is often used in TACE procedures (doxorubicin DEBs are usually referred to in the trade as DEBDOX). The central loading cavity 812, 822 is also filled with a contrast agent which facilitates proper imaging of the beads in an imaging procedure, for instance contrast agents based on Iodine, Gadolinium or other substances known to the skilled person. The contrast agent preferably has a k-edge that is detectable by spectral CT imaging energies. The DEBs are introduced into a patient's bloodstream and delivered to a tissue of interest, where the drug is slowly released from the DEBs 81, 82.

As mentioned in the introduction, a size of the DEB determines the maximum drug load and which vessels can be effectively embolized. In general, larger sized DEBs can carry a higher drug load, but cannot embolize smaller vessels, particularly those inside tumors. Smaller sized DEBs can embolize smaller vessels, but carry a lower drug load and cannot effectively embolize larger vessels, such as tumor feeding vessels.

Figure 3:
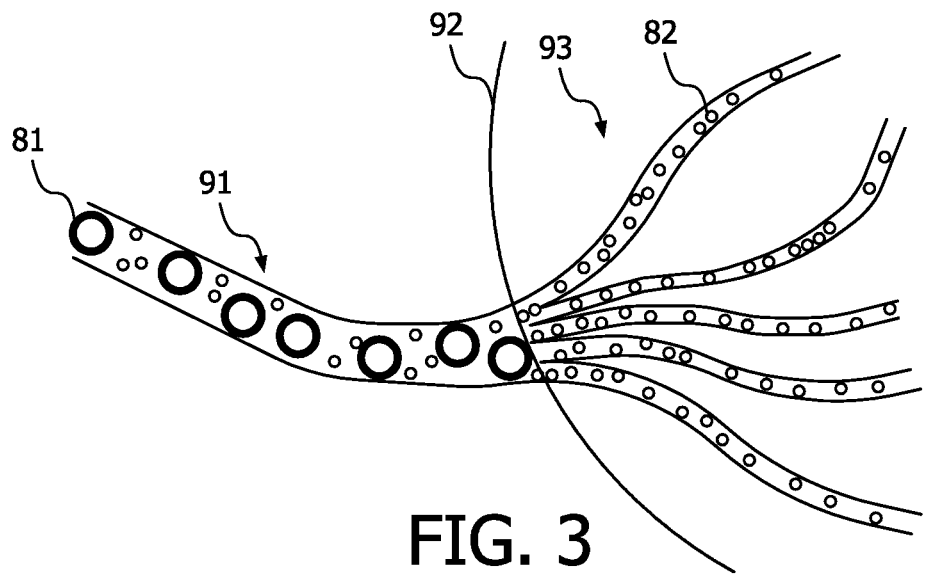
FIG. 3 shows a schematic representation of arteries in a region of interest to which two differently sized DEBs were administered.

An insight that lies at the basis of many aspects of this invention is that a mixture, or a subsequent administration, of differently sized DEBs 81, 82 introduced to a patient overcomes these drawbacks. This is illustrated schematically in FIG. 3. This figure shows part of a blood vessel system of a patient including a feeding vessel 91 to a tumor, for instance an hepatic artery leading to a liver tumor. At a tumor rim 92 the feeding vessel 91 splits up into many smaller tumor core vessels 93. In this embodiment two differently sized DEBs were administered to the patient: large DEBs 81 with an exemplary diameter of around 300 microns and small DEBs 82 with an exemplary diameter of 75 microns. DEBs with other diameters and a larger number of differently sized DEBs are of course also possible, depending on the different vessel sizes and can be chosen by a physician on a case-by-case basis. The small DEBs 82 are able to embolize the small tumor core vessels 93 to release the drug there locally. While small DEBs 82 are also present in the feeding vessel 91, they do not effectively embolize said feeding vessel 91. The large DEBs however do embolize the feeding vessel 91 very well. The large DEBs 81 are too large to enter the tumor core vessels 93 and will, in this embodiment, not pass beyond the tumor rim 92. A good embolization of all relevant vessels in around the tumor is obtained.

In a further embodiment of the present invention the large DEBs 81 and the small DEBs 82 are loaded with different drugs. For example, the tumor core 93 is typically hypoxic and so hypoxia-activated pro-drugs like TH-302 may have a greater efficacy in tumor kill, while traditional chemotherapy for the area of the tumor rim 92 could be used where there is normoxia. As such, the tumor can be treated more effectively by targeting different parts of the tumor with different drugs. Potentially a better targeted dosage regime of large and small DEBs 81, 82 may result in a more precise drug dosage and therefore less side effects may be experienced by the patient. In an embodiment of the present invention the small DEBs 82 are loaded with hypoxia-activated pro-drugs like TH-302 and the large DEBs 82 are loaded with traditional chemotherapy drugs. The two (or more) chemotherapeutic drugs, may be used either in combination (first drug+second drug) or as a tumor microenvironment activated pro-drug (the first drug is activated in tumor microenvironment and promotes efficacy of the second drug). The first and second drug may have different concentrations. An alternative option is that the first drug and second drug are the same, but that the concentration is bead size specific. In all cases, other properties than the concentration (e.g. drug release rate) may be chosen to be different for different bead sizes.

In a further embodiment of the present invention the large DEBs 81 and the small DEBs 82 are loaded with different contrast agents. This facilitates imaging the large DEBs 81 and the small DEBs 82 separately with energy resolving imaging systems, such as spectral CT and k-edge imaging techniques. This avoids separation of the contrast agents from the DEBs 81,82 because the contrast agent is present within the bead. As such, it is possible to more accurately determine if the DEBs 81, 82 have reached their predetermined destination and if the vessels are properly embolized. When it is known how many of the DEBs actually reach the intended region of interest, a more precise dosage regime, e.g. lower doses and therefore less side effects, may be implemented.

Figure 4:
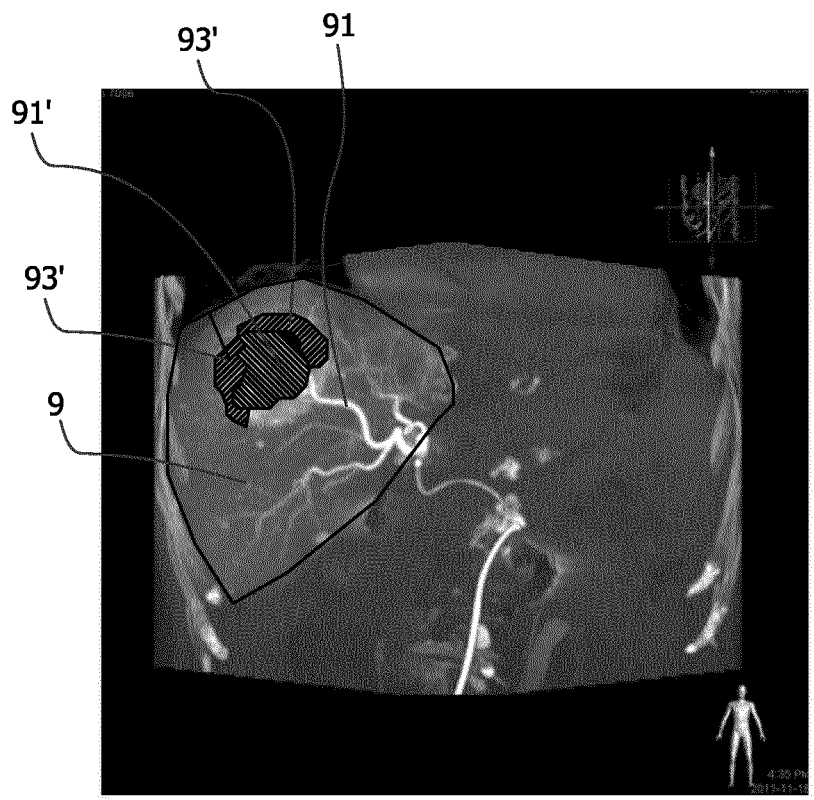
FIG. 4 shows a simulated depiction of a CT reconstruction of a liver area in a patient with an overlaid illustration of a size selective bead concentration.

FIG. 4 depicts an exemplary, simulated CT reconstruction of a part of a patient's body including a liver 9. The liver 9 has a tumor, which comprises actual tumor mass containing tumor core vessels 93 and a blood supply area, which comprises at least one feeding vessel 91. Large DEBs 81 and small DEBs 82 were previously administered to the patient using injecting device 7. The liver 9 area was then imaged with a spectral CT imaging device 10. In this embodiment the large DEBs 81 were loaded with a different contrast agent (e.g. an Iodine based contrast agent) than the small DEBs 82 (e.g. a Gadolinium based contrast agent). Through k-edge imaging both contrast agents are individually identified and, as such, the location of the large DEBs 81 and the small DEBs 82 in the tumor area is known and can be depicted, for instance, by presenting this as an overlay over the CT image. In FIG. 4 this is depicted as hatched areas for the location 93' of the small DEBs 83 and a 90 degrees tilted (compared to the small DEB area 93') hatched area for the location of the large DEBs 81. A physician will immediately notice that the small DEBs 83 have penetrated into the tumor core, while the large DEBs 81 have penetrated the blood supply area.

Inherently radio-opaque DEBs provides direct visualization of bead deposition. This is a marked improvement in image-guided feedback. A degree of DEB radio-opacity is directly related to the drug dose. Multi-energy imaging, such as spectral CT, has the ability to image and quantitatively measure the DEB radio-opacity and thus the actual drug dose at the tumor site. A DEB concentration determiner 11 is configured to determine the drug concentration from obtained image data of the areas embolized by DEBs. This is of extremely high added value to TACE procedures. As mentioned previously, in TACE procedures it is actually very difficult to determine the drug dose that actually reaches the tumor. It is well known in chemotherapy medicine that a sufficient drug dose concentration is needed for tumor kill, but that many of the drugs unfortunately have severe side effects. Therefore it is crucial to find an optimal balance between sufficient drugs to treat the tumor, but not too much to severely discomfort an already weakened patient. With the elements of the present invention the drug dose at the tumor location and surrounding areas may be much more accurately and reliably determined. This will assist the physician to better determine an optimal dose and increase tumor treatment efficacy, while keeping side effects under control as much as possible, which increases the patient's quality of life during the treatment and because of that it might also improve treatment efficacy.

FIG. 5A depicts a schematic flow chart of a TACE method comprising the steps of administering 101 first DEBs containing at least a first drug and a first contrast agent to a region of interest comprising a tumor, and administering 102 second DEBs containing at least a second drug and a second contrast agent to the region of interest, wherein the first DEBs have a larger diameter than the second DEBs. Preferably the first and second DEBs contain different drugs and/or contrast agents.

FIG. 5B depicts a schematic flow chart of a method for determining a delivered drug dose concentration in a region of interest comprising a tumor, comprising the steps of obtaining 201 a first image data set by imaging the region of interest with an x-ray imager operating at a first x-ray radiation energy and determining 203, from the first image data set, a first drug concentration delivered to the region of interest by first DEBs containing at least a first drug and a first contrast agent, obtaining 202 a second image data set by imaging the region of interest with an x-ray imager operating at a second x-ray radiation energy and determining 204, from the second image data set, a second drug concentration delivered to the region of interest by second DEBs containing at least a second drug and a second contrast agent, wherein the first DEBs have a larger diameter than the second DEBs.

An imaging system 1 arranged to obtain a first image data set of the region of interest with at least a first x-ray radiation energy and a second image data set of the region of interest with at least a second x-ray radiation energy, such as a CT imaging system or a cone-beam CT (CBCT) imaging system, is particularly suitable to determine concentrations. When a concentration of the first and second drugs are know for the region (or respective regions) of interest, this provides an excellent indication of the actually delivered drug dose to the region(s) of interest. A ratio of contrast to drug concentration for every bead size is necessary to determine the specific drug dose. In imaging systems which do not obtain image data at more than one energy level, e.g. MR imaging systems, it is possible to distinguish microspheres of different sizes that contain different contrast agents, but not to quantify the drug dose. After all, it is the chemotherapy drug (or drugs) and not he contrast medium having the tumoricidal effect. And also, the signal intensity from, for instance, MR imaging is in arbitrary units, whereas the multi-energy based imaging provide absolute measurement units of concentration. This is an inherent technical advantage of multi-energy imaging such as spectral CT or CBCT imaging. Therefore, this not only provides absolute measurement metrics, the TACE system of the present invention allows for inter-patient visualization and comparison of drug delivery, which is important for image guidance and follow-up and for assessing efficacy of treatment.

Preferably the x-ray imager operates at a first pair of x-ray energies to obtain the first image data set and at a second pair of x-ray energies to obtain the second data set, since this is a prerequisite for k-edge imaging of a contrast agent. Preferably the image data sets are reconstructed to visual data and displayed to a physician 205. The visual data may comprise the location of the differently sized DEBs and/or drug concentration at specific locations. This may be done by overlaying a CT image with additional information, such as hatched or colored areas, numerical data on or with the reconstructed CT image or any other suitable way of displaying visual data known in the art.

The present invention also relates to an imaging system that is configured to determine a drug concentration in a tumor after a TACE procedure. Said system comprises an imaging system 10, preferably a spectral CT imaging system that can obtain data sets of areas of interests that are embolized by at least two differently sized DEBs. These DEBs may contain different drugs and/or contrast agents. The system further comprises a concentration determiner 11 to determine the drug concentrations from the first and second image data sets of each of the differently sized DEBs at a region of interest, such as a tumor area including feeding areas and the tumor core. Preferably the image data sets are reconstructed in a reconstructor to visual data that may be presented to a physician on a display unit. The visual data may comprise the location of the differently sized DEBs an/or drug concentration at specific locations. This may be done by overlaying a CT image with additional information, such as hatched or colored areas, numerical data on or with the CT image or any other suitable way of displaying visual data known in the art.

The present invention further relates to a computer program product for determining a drug concentration in a tumor after a transarterial chemoembolization (TACE) procedure in which at least a first drug and a second drug were delivered to the region of interest, comprising instructions to execute the steps of determining a first and a second drug concentration a first and second image data set of the region of interest when the computer program product is run on the computer. Preferably the first and second image data set were obtained at different x-ray radiation energies, such as with a spectral CT imaging device. Preferably the first and second drugs were delivered to the region of interest by at least two differently sized DEBs, preferably containing different drugs and/or contrast agents.

FIG. 6 presents a schematic representation of a kit-of-parts 300 comprising a quantity 301 of first DEBs containing at least a first drug and a first contrast agent; and a quantity 302 of second DEBs containing at least a first drug and a first contrast agent. Preferably the first and second DEBs contain different drugs and/or contrast agents. Either of the first or second DEBs may be DOXDEBs. The first and second quantity of DEBs may be such that they are already provided in a desired quantity ratio. The first and second DEBs may be provided separately or as a pre-mixed mixture.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system for a transarterial chemoembolization of a region of interest comprising a tumor, comprising:
    an injecting device arranged to introduce into the region of interest first drug-eluting microsphere beads containing at least a first drug and a first contrast agent and to introduce into the region of interest second drug-eluting microsphere beads containing at least a second drug that is different from the first drug and a second contrast agent;
    an imaging system arranged to obtain a first image data set of the region of interest with at least a first x-ray radiation energy that corresponds to the first contrast agent, and a second image data set of the region of interest with at least a second x-ray radiation energy that corresponds to the second contrast agent, wherein the first image data set comprises the first contrast agent, and the second image data set comprises the second contrast agent; and processor circuitry configured to determine, based on the first contrast agent, a first drug concentration from the first image data set and determine, based on the second contrast agent, a second drug concentration from the second image data set, wherein the first drug-eluting microsphere beads have a larger diameter than the second drug-eluting microsphere beads.

2. The system according to claim 1, wherein the imaging system is a spectral computed tomography imaging system arranged to simultaneously obtain the first image data and second image data.

3. The system according to claim 1, wherein the first drug-eluting microsphere beads have a size to prevent penetration into tumor core vessels, and the size allowing penetration into an upper stream of tumor core vessels, and
the second drug-eluting microsphere beads have a size to allow penetration into tumor core vessels, thereby allowing release of the second contrast agent of the second drug-eluting microsphere beads into tumor core vessels.

4. The system according to claim 1, wherein the first contrast agent is different from the second contrast agent.

5. The system according to claim 1, wherein the at least first x-ray radiation energy corresponds to a K-absorption edge of the first contrast agent and the at least second x-ray radiation energy corresponds to a K-absorption edge of the second contrast agent.

6. The system of claim 1, wherein the imaging system is configured to obtain the first image data set at a time when the first contrast agent is in an upper stream of tumor core vessels,
the imaging system is configured to obtain the second image data set at a time when the second contrast agent that has a different radiation absorption characteristic than the first contrast agent is in tumor core vessels,
the processor circuitry is configured to determine the first drug concentration based on the first contrast agent that is in the upper stream of tumor core vessels, and
the processor circuitry is configured to determine the second drug concentration based on the second contrast agent that is in the tumor core vessels.

7. The system of claim 1, wherein the imaging system is configured to obtain the first image data set at a time:
when the first contrast agent is in the upper stream of tumor core vessels, and
when the second contrast agent that has a different radiation absorption characteristic than the first contrast agent is in tumor core vessels.

8. The system of claim 1, wherein the processor circuitry is configured to configure a display to display:
a first location of at least one of the first drug concentration and the first drug-eluting microsphere beads, the first location being overlayed over the upper stream of tumor core vessels on a computerized tomography (CT) image, and
a second location of at least one of the second drug concentration and the second drug-eluding mircosphere beads, the second location being overlayed over the tumor core vessels on the same CT image.

9. A method for determining a delivered drug dose concentration in a region of interest comprising a tumor, comprising:
obtaining a first image data set by imaging the region of interest with an x-ray imaging device operating at least at a first x-ray radiation energy that corresponds to a first contrast agent, wherein the first image data set comprises the first contrast agent;
determining, from the first contrast agent of the first image data set, a first drug concentration delivered to the region of interest by the first drug-eluting microsphere beads containing at least a first drug and the first contrast agent;
obtaining a second image data set by imaging the region of interest with an x-ray imaging device operating at least at a second x-ray radiation energy that corresponds to a second contrast agent, wherein the second image data set comprises the second contrast agent; and
determining, from the second contrast agent of the second image data set, a second drug concentration delivered to the region of interest by the second drug-eluting microsphere beads containing at least a second drug and the second contrast agent, wherein the first drug-eluting microsphere beads have a larger diameter than the second drug-eluting microsphere beads, and wherein the second drug is different from the first drug.

10. The method according to claim 9, wherein the first image data and the second image data are obtained simultaneously.

11. The method according to claim 9, wherein the first drug-eluting microsphere beads have a size to prevent penetration into tumor core vessels, and the size allowing penetration into an upper stream of tumor core vessels, and
the second drug-eluting microsphere beads have a size to allow penetration into tumor core vessels, thereby allowing release of the second contrast agent of the second drug-eluting microsphere beads into tumor core vessels.

12. The method according to claim 9, wherein the first contrast agent is different from the second contrast agent.

13. The method according to claim 9, wherein the at least first x-ray radiation energy corresponds to a K-absorption edge of the first contrast agent and the at least second x-ray radiation energy corresponds to a K-absorption edge of the second contrast agent.

14. The method of claim 9, wherein the obtaining of the first image data set includes obtaining the first image data set at a time when the first contrast agent is in an upper stream of tumor core vessels,
the obtaining of the second image data set includes obtaining the second image data set at a time when the second contrast agent that has a different radiation absorption characteristic than the first contrast agent is in tumor core vessels,
determining of the first drug concentration includes determining the first drug concentration based on the first contrast agent that is in the upper stream of tumor core vessels, and
determining of the second drug concentration includes the second drug concentration based on the second contrast agent that is in the tumor core vessels.

15. The method of claim 9, wherein the obtaining of the first image data set includes obtaining the first image data set at a time:
when the first contrast agent is in the upper stream of tumor core vessels, and when the second contrast agent that has a different radiation absorption characteristic than the first contrast agent is in tumor core vessels.

16. The method of claim 9, further comprising displaying:

a first location of at least one of the first drug concentration and the first drug-eluting microsphere beads, the first location being overlayed over the upper stream of tumor core vessels on a computerized tomography (CT) image, and a second location of at least one of the second drug concentration and the second drug-eluting microsphere beads, the second location being overlayed over the tumor core vessels on the same CT image.

\* \* \* \* \*